US010184924B2

(12) United States Patent
Hitchcock et al.

(10) Patent No.: US 10,184,924 B2
(45) Date of Patent: Jan. 22, 2019

(54) METHOD AND SYSTEM FOR DECOUPLING A CAPILLARY COLUMN FROM A GAS CHROMATOGRAPHY-MASS SPECTROMETRY (GC-MS) SYSTEM

(71) Applicant: Thermo Finnigan LLC, San Jose, CA (US)

(72) Inventors: James M. Hitchcock, Pflugerville, TX (US); George B. Guckenberger, Austin, TX (US)

(73) Assignee: Thermo Finnigan LLC, San Jose, CA (US)

( * ) Notice: Subject to any disclaimer, the term of this patent is extended or adjusted under 35 U.S.C. 154(b) by 148 days.

(21) Appl. No.: 15/271,138

(22) Filed: Sep. 20, 2016

(65) Prior Publication Data

US 2017/0010244 A1    Jan. 12, 2017

Related U.S. Application Data

(62) Division of application No. 14/446,041, filed on Jul. 29, 2014, now Pat. No. 9,463,534.

(51) Int. Cl.
*G01N 30/72* (2006.01)
*H01J 49/04* (2006.01)
*B23P 6/00* (2006.01)

(52) U.S. Cl.
CPC ............ *G01N 30/7206* (2013.01); *B23P 6/00* (2013.01); *H01J 49/0422* (2013.01); *H01J 49/0427* (2013.01); *Y10T 29/4973* (2015.01); *Y10T 29/49815* (2015.01)

(58) Field of Classification Search
CPC .............. G01N 30/7206; H01J 49/0427; H01J 49/0422; B23P 6/00; Y10T 29/4973; Y10T 29/49815
See application file for complete search history.

(56) References Cited

U.S. PATENT DOCUMENTS

| 4,662,914 A | 5/1987 | Hansen et al. |
| 4,985,625 A | 1/1991 | Hurst |
| 7,260,978 B2 | 8/2007 | Miyagawa |
| 7,709,790 B2 | 5/2010 | Guckenberger et al. |
| 9,228,984 B2 * | 1/2016 | Lu ..................... G01N 30/461 |

(Continued)

FOREIGN PATENT DOCUMENTS

| JP | 2004-139911 | 5/2004 |
| WO | 2009/123914 A1 | 10/2009 |

*Primary Examiner* — John C Hong
(74) *Attorney, Agent, or Firm* — David A. Schell

(57) ABSTRACT

A column-sealing tool is provided for use during decoupling of a capillary column from a gas chromatography-mass spectrometry (GC-MS) system. The column-sealing tool includes an engagement structure for removably securing the column-sealing tool within a high vacuum enclosure of the GC-MS system, at a location between a high vacuum end of a transfer line and a mass analyzer of the GC-MS system. Additionally, the column-sealing tool includes a sealing element that is actuatable between a non-sealing position and a sealing position. During use the sealing element forms a secondary vacuum seal with the first end of the transfer line when the column-sealing tool is inserted into the GC-MS system and when the sealing element is in the sealing position.

8 Claims, 8 Drawing Sheets

(56) References Cited

U.S. PATENT DOCUMENTS

| | | | |
|---|---|---|---|
| 2007/0108381 A1* | 5/2007 | Kuypers | H01J 49/0404 250/288 |
| 2010/0223978 A1 | 9/2010 | McCauley | |
| 2011/0174969 A1 | 7/2011 | Seyfarth | |
| 2013/0256523 A1 | 10/2013 | Steiner et al. | |

* cited by examiner

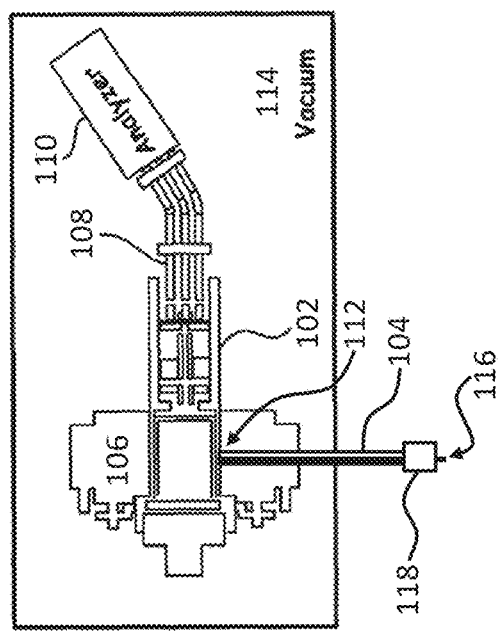
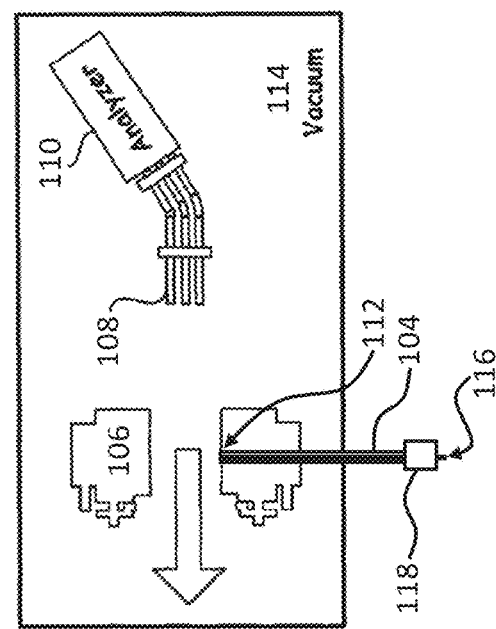
FIG. 1A
FIG. 1B

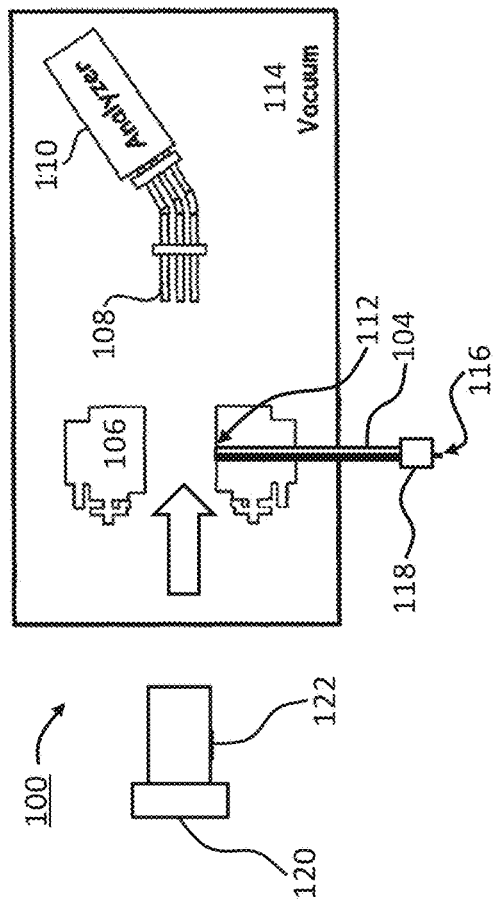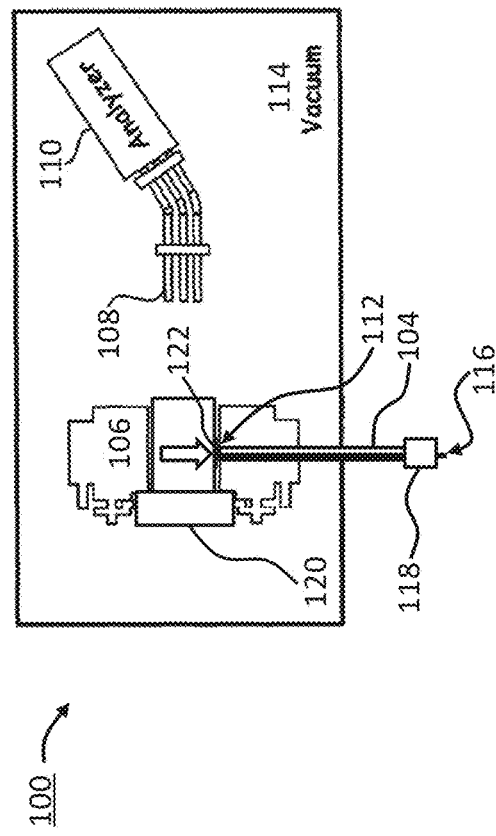

METHOD AND SYSTEM FOR DECOUPLING A CAPILLARY COLUMN FROM A GAS CHROMATOGRAPHY-MASS SPECTROMETRY (GC-MS) SYSTEM

FIELD OF THE INVENTION

The invention relates generally to charged particle analyzers, and more particularly to a method and system for decoupling a capillary column from a gas chromatography-mass spectrometry (GC-MS) system without venting a high vacuum enclosure that at least partially contains the capillary column.

BACKGROUND OF THE INVENTION

Column maintenance and/or replacement is a routine process in the field of mass spectrometry, typically requiring the operator to cool down the mass spectrometer and vent the high vacuum chamber to atmospheric pressure prior to decoupling the capillary column from the system. This process is time consuming, as the operator must wait for the system to cool, vent and then re-thermalize after startup before continuing productive work with the instrument. For instance, each time this process is performed on a quadrupole mass analyzer an estimated five hours of instrument time is lost. Further, this time is increased for some analytical instruments, which require ultra high vacuum pressure that can only be achieved with several hours of "bake out" at elevated temperature.

To avoid the above-noted disadvantages, many operators have installed "no vent" column changing systems. These systems typically require an additional restrictor to be installed in the column path, as well as a gas tank to protect against contamination during column maintenance. Unfortunately, the use of a "no vent" system prevents the operator from positioning the end of the capillary column immediately adjacent to the ionization source. As such, in addition to adding complexity, these "no vent" systems also have a tendency to introduce active sites in the column path, which results in reduced response to injected sample and poor linearity in calibration curves.

An alternative, albeit more risky, method of replacing the capillary column in GC-MS systems requires the operator to remove the current column and expose the vacuum chamber to a high flow of ambient air while quickly installing the new column. In addition to placing strain on the pumping system and causing oxidation of heated components, this method also risks introducing ferrule particulates and dust into the ion source and lens assembly as well as causing damage to the columns. The success of this method is strongly dependent on operator skill, experience and agility.

Another difficulty that is encountered during routine column maintenance is ensuring that the outlet end of the capillary column is positioned properly, every time the column is replaced. Proper positioning of the column requires a high level of operator skill as well as the use specialized tools. Failure to properly position the column when it is reattached may affect the reproducibility and reliability of analytical results that are obtained using the GC-MS system.

It would be beneficial to provide a method and system that overcomes at least some of the above-mentioned limitations and drawbacks of the prior art.

SUMMARY OF EMBODIMENTS OF THE INVENTION

In accordance with an aspect of at least one embodiment of the invention, there is provided a method for decoupling a capillary column from a gas chromatography-mass spectrometry (GC-MS) system, comprising: removing as a unit from the GC-MS system an ion source that is disposed, prior to removal, between a high vacuum end of a transfer line and a mass analyzer of the GC-MS system; inserting in place of the ion source a column-sealing tool having a sealing element that is actuatable between a non-sealing position and a sealing position, the sealing element being maintained in the non-sealing position during inserting; actuating the sealing element from the non-sealing position to the sealing position to form a secondary vacuum seal with the high vacuum end of the transfer line; subsequent to establishing the secondary vacuum seal, breaking a primary vacuum seal between the capillary column and an end of the transfer line that is opposite the high vacuum end; and withdrawing the capillary column away from and out of the transfer line.

After breaking the primary vacuum seal a gas flow rate through the secondary vacuum seal does not exceed 100 ml/minute.

In certain implementations the gas flow rate through the secondary vacuum seal does not exceed 50 ml/minute.

In certain implementations the gas flow rate through the secondary vacuum seal does not exceed 10 ml/minute.

In accordance with an aspect of at least one embodiment of the invention, there is provided a system for decoupling a capillary column from a gas chromatography-mass spectrometry (GC-MS) system, comprising: a transfer line having a first end that is disposed within a high vacuum enclosure of the GC-MS system and that is aligned with a removable ion source sub-assembly of the GC-MS system, and having a second end that is opposite the first end, the second end being sized to receive an outlet end of a capillary column; a primary vacuum seal element for forming a primary vacuum seal between the capillary column and the second end of the transfer line, the outlet end of the capillary column being positioned within the high vacuum enclosure and in fluid communication with the removable ion source when the primary vacuum seal is formed; and a column-sealing tool configured to be inserted into the GC-MS system, subsequent to removal of the removable ion source sub-assembly, at a location between the first end of the transfer line and a mass analyzer of the GC-MS system, the column-sealing tool comprising a sealing element that is actuatable between a non-sealing position and a sealing position; and an actuator for selectably actuating the sealing element between the non-sealing position and the sealing position, wherein the sealing element forms a secondary vacuum seal with the first end of the transfer line when the column-sealing tool is inserted into the GC-MS system and when the sealing element is in the sealing position.

In accordance with an aspect of at least one embodiment of the invention, there is provided a column-sealing tool for use during decoupling of a capillary column from a gas chromatography-mass spectrometry (GC-MS) system, the column-sealing tool comprising; an engagement structure for removably securing the column-sealing tool within a high vacuum enclosure of the GC-MS system and at a location between a high vacuum end of a transfer line and a mass analyzer of the GC-MS system; and a sealing element that is actuatable between a non-sealing position and a sealing position; wherein the sealing element forms a secondary vacuum seal with the first end of the transfer line when the column-sealing tool is inserted into the GC-MS system and when the sealing element is in the sealing position.

In accordance with an aspect of at least one embodiment of the invention, there is provided a column-sealing tool for use during decoupling of a capillary column from a gas chromatography-mass spectrometry (GC-MS) system, the column-sealing tool comprising; an engagement structure for removably securing the column-sealing tool within a high vacuum enclosure of the GC-MS system and at a location between a high vacuum end of a transfer line and a mass analyzer of the GC-MS system; and a wheel-shaped sealing element rotatably mounted to a body of the column-sealing tool via an axle structure; wherein the sealing element is disposed for forming a secondary vacuum seal with the first end of the transfer line when the column-sealing tool is inserted into the GC-MS system and when the sealing element is in the sealing position.

BRIEF DESCRIPTION OF THE DRAWINGS

The instant invention will now be described by way of example only, and with reference to the attached drawings, wherein similar reference numerals denote similar elements throughout the several views, and in which:

FIG. 1A is a simplified diagram showing a general assembled GC-MS system with a removable ion source disposed adjacent to a transfer line.

FIG. 1B is a simplified diagram showing the system of FIG. 1A with the removable ion source removed.

FIG. 1C is a simplified diagram showing the system of FIG. 1A prior to inserting a column-sealing tool.

FIG. 1D is a simplified diagram showing the system of FIG. 1A with the column-sealing tool disposed adjacent to the outlet end of the transfer line, but prior to forming a seal between a sealing element of the column-sealing tool and the transfer line.

DETAILED DESCRIPTION OF EMBODIMENTS OF THE INVENTION

Figure 1E:
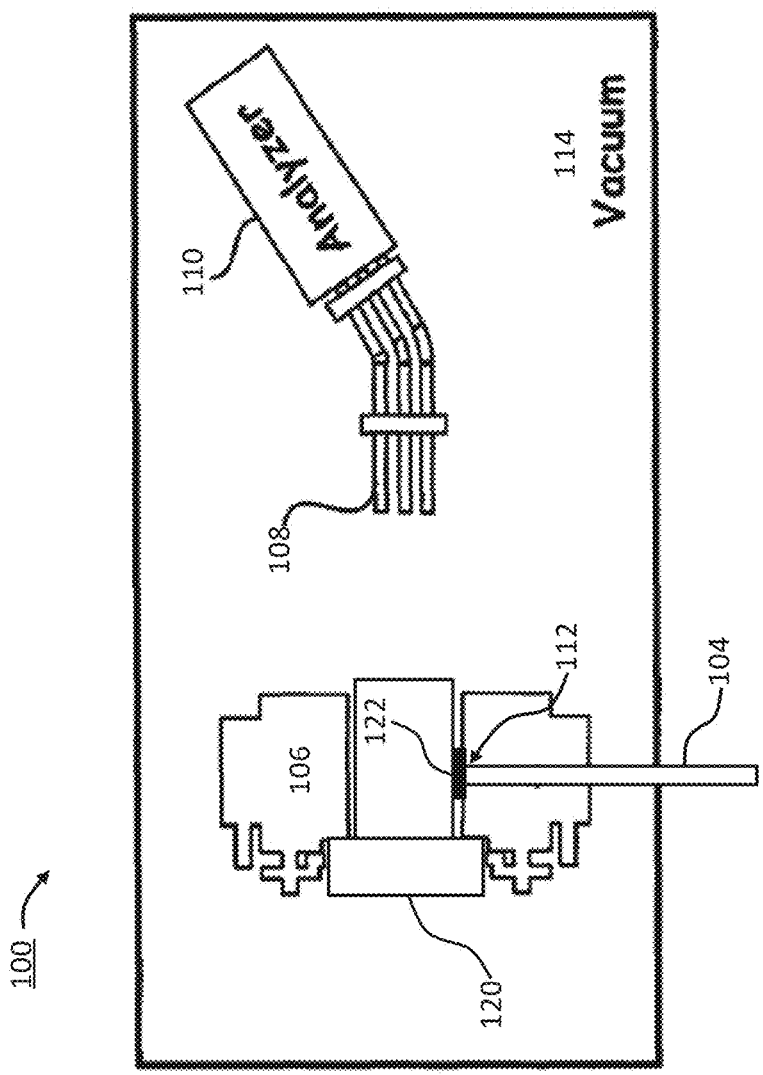
FIG. 1E is a simplified diagram showing the system of FIG. 1A after the sealing element of the column-sealing tool is actuated into a sealing position.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Moreover, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Certain markets that use mass spectrometers are focused on running as many samples through the instrument as possible. The time required to vent, disassemble, clean, reassemble, and then pump down the system back to operating pressures is costly and time inefficient. However, a significant amount of time/cost savings can be obtained in the operation if the venting and pump down aspects of maintenance can be removed from the equation. The drawings and related text disclose methods, systems and apparatus that address such a market need. In a convenient manner, a secondary vacuum seal is established prior to breaking the primary vacuum seal in a gas chromatography-mass spectrometry (GC-MS) system, such as for instance during routine column maintenance or column replacement. The said methods, systems and apparatus allow the operator to decouple the capillary column from the GC-MS system for maintenance and/or replacement without having to vent and/or cool the instrument.

Referring now to FIG. 1A, shown a simplified diagram of a general assembled GC-MS system 100 with a removable ion source 102, which is disposed adjacent to a transfer line 104. By way of a specific and non-limiting example, the removable ion source 102 is configured in accordance with the teaching of U.S. Pat. No. 7,709,790, which issued on May 4, 2010, and the entire contents of which are incorporated herein by reference. The removable ion source 102 and other components of the system 100, which include but are not limited to a heater block 106, an ion guide 108 and an analyzer 110, as well as the outlet (high vacuum) end 112 of the transfer line 104, are contained within a common or segmented vacuum enclosure 114. An end section of a capillary column 116 extends through the transfer line 104, all the way to the outlet end 112 of the transfer line 104 within the vacuum enclosure 114. A ferrule 118, or another suitable element, forms a primary vacuum seal between the capillary column 116 and the transfer line 104. In this way, sample that is injected onto the capillary column 116 can be introduced into the vacuum enclosure 114, where it is ionized using the ion source 102 prior to being transported through the ion guide 108 to the analyzer 110.

It is to be appreciated that the single analyzer 110, as shown in FIG. 1A, can include a variety of single stage analyzer systems capable of mass spectrometry, such as, for example, a time-of-flight (TOF) device, a linear ion trap (LIT), magnetic and electrostatic analyzers, a quadrupole, an ion cyclotron resonance (ICR) instrument, an orbitrap, or a Fourier Transform Mass Spectrometer (FTMS). Moreover, the embodiments of the present invention can also be utilized in a tandem mass spectrometer with more than one analyzer (known as tandem in space), as known to those of ordinary skill in the art. For example, one mass analyzer can isolate one precursor from many precursors entering a mass analyzer, after which the isolated precursor is collided with a gas within a collision cell causing fragmentation of the isolated precursor. A second mass analyzer then can catalog the fragments produced from the fragmented isolated precursor.

As is shown in FIG. 1B, the ion source 102 is removable from the GC-MS system 100 as a unit. In particular, an insertion/retraction (I/R) tool (not illustrated) is used to engage a locking feature (or engagement structure) at end of the ion source 102, and subsequently retract the ion source 102 out of the system 100 along the direction of the block arrow in the drawing. A valve system is used to avoid the need to vent the vacuum enclosure 114 during insertion of the tool and removal of the ion source 102. As is shown in FIG. 1B, removal of the ion source 102 from the system 100 leaves a void immediately adjacent to the outlet end 112 of transfer line 104. The primary vacuum seal is maintained between the column 116 and the transfer line 104, using the ferrule 118, such that ambient atmosphere cannot pass through the transfer line 104 and enter the vacuum enclosure 114.

Referring now to FIG. 1C, shown is the system 100 and a column-sealing tool 120. The column-sealing tool 120 is configured to fit into the void immediately adjacent to the outlet end 112 of transfer line 104, when the ion source 102 is removed. Column-sealing tool 120 has a sealing element 122 that is arranged on the column-sealing tool 120 such that the sealing element 122 is opposite the outlet end 112 of the transfer line 104 when the column-sealing tool 120 is fully inserted into the void. In particular, FIG. 1C depicts the sealing element 122 in a non-sealing position during insertion of the column-sealing tool 120 into the void along the direction of the block arrow. A tool, such as for instance the same I/R tool that is used to remove the ion source 102, is used to engage locking features at one end of the column-sealing tool 120 and insert the column-sealing tool 120 through the not illustrated valve system and into the void. Once in the fully inserted position, as is shown in FIG. 1D, the sealing element 122 is actuated into a sealing position. For instance, at least a portion of the sealing element 122 is actuated along the direction of the block arrow in the diagram and toward the outlet end 112 of the transfer line 104. Optionally, a linear actuator or a rotational actuator serves to actuate the at least a portion of the sealing element 122 into the sealing position.

Referring now to FIG. 1E, shown is the column-sealing tool 120 fully inserted into the void immediately adjacent to the transfer line 104, and with the sealing element 122 in the sealing position. The sealing element forms a secondary vacuum seal against the outlet end 112 of the transfer line 104. It is not essential to form a secondary vacuum seal that is of the same quality as the primary vacuum seal. In particular, relatively small leaks can be tolerated for a short period of time without placing undue stress on the pumping system. Of course, the maximum gas flow rate that can be tolerated through the secondary vacuum seal depends upon, inter alia, how long it takes the operator to replace the column and re-establish the primary vacuum seal. By way of a specific and non-limiting example, the secondary vacuum seal limits the flow of gas into the vacuum enclosure 114 to less than 100 ml/minute. In certain implementations the secondary vacuum seal limits the flow of gas into the vacuum enclosure 114 to less than 50 ml/minute. In certain implementations the secondary vacuum seal limits the flow of gas into the vacuum enclosure 114 to less than 10 ml/minute. It is to be understood however, that different gases may impose different demands on the quality of the secondary vacuum seal.

Of course, FIGS. 1A-E depict the steps that are performed during decoupling of the capillary column 116 from the GC-MS system 100, without venting or cooling the instrument. In order to replace the column 116 after routine maintenance, or in order to couple a different capillary column to the GC-MS system 100, substantially the same steps are performed in the reverse order. Briefly, one end of the capillary column 116 is inserted into the end of the transfer line 104 that is external to the vacuum enclosure 114 and opposite the outlet end 112. The capillary column 116 is advanced through the transfer line 104 until it makes contact with the sealing element 122 of the column-sealing tool 120. Advantageously, the sealing element 122 acts as a "stop" for the column and ensures accurate and precise positioning of the capillary column 116 without the need to use specialized tools or provide extensive operator training. Once the column is in the correct position, the ferrule 118 is tightened and the primary vacuum seal is re-established. The sealing element 122 is then actuated to the non-sealing position, thereby breaking the secondary vacuum seal and permitting the column-sealing tool to be removed from the GC-MS system via the valve system. Finally, the ion source 102 is inserted into the GC-MS system via the valve system, and productive operation of the GC-MS system may resume.

Figure 2A:
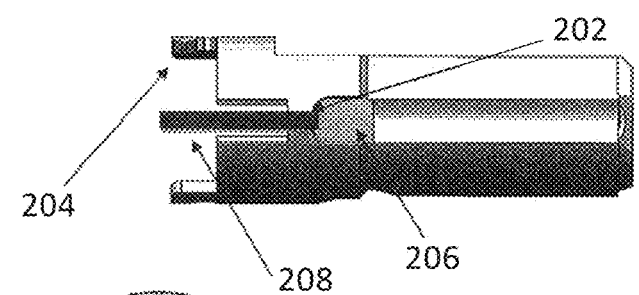
FIG. 2A is a simplified side view showing a column-sealing tool according to an embodiment of the invention.
Figure 2B:
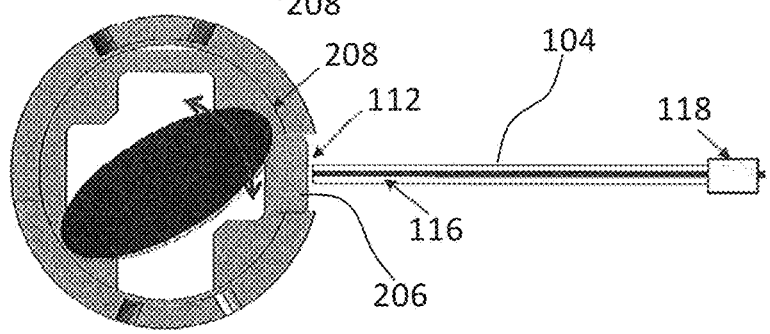
FIG. 2B is a simplified end view showing the column-sealing tool of FIG. 2A disposed adjacent to a transfer line, and prior to forming a seal between the sealing element and the transfer line.
Figure 2C:
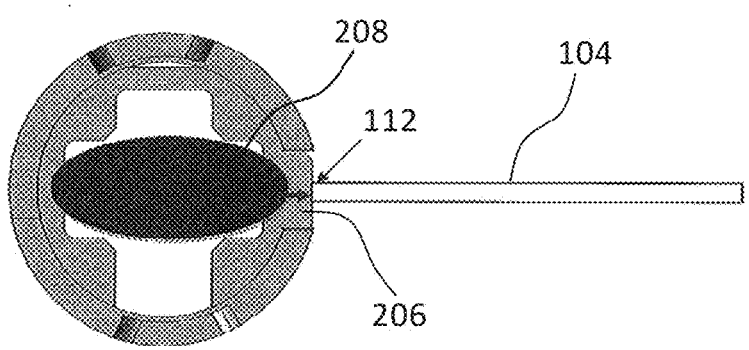
FIG. 2C is a simplified end view showing the column-sealing tool of FIG. 2A disposed adjacent to a transfer line, and subsequent to forming a seal between the sealing element and the transfer line.

Referring now to FIGS. 2A-C, shown are selected features of a column-sealing tool 200 according to an embodiment of the invention. FIG. 2A is a side view showing the general shape of the column-sealing tool 200, which is configured to fit into the void immediately adjacent to the outlet end 112 of the transfer line 104 of system 100. The column-sealing tool 200 includes an optional alignment key 202, which is used to ensure correct alignment with the transfer line 104 when the tool 200 is inserted into the system 100. Locking features 204 (or engagement structure) are provided at one end of the column-sealing tool 200, for engaging complementary features of a not-illustrated I/R tool, which is used for inserting and retracting the column-sealing tool 200. Also shown in FIG. 2A is a sealing element 206, which is fabricated from a malleable, high temperature material. By way of a few specific and non-limiting examples, the sealing element 206 is fabricated from one of silicone rubber, a fluorinated elastomer, and a polyimide.

The sealing element 206 is actuatable between a non-sealing position (as shown in FIG. 2B) and a sealing position (as shown in FIG. 2C). The column-sealing tool includes an actuator, in this specific example a rotational actuator 208, for actuating the sealing element 206 between the non-sealing and sealing positions. In particular, rotating the actuator 208 causes the sealing element 206 to deform and thereby forces a portion of the sealing element 206 to move radially outward and into engagement with the outlet end 112 of transfer line 104. As shown in FIGS. 2B and 2C, the ferrule 118 may be removed after the sealing element 206 engages the outlet end 112 of transfer line 104 to form a secondary vacuum seal, and the capillary column 116 may then be decoupled from the system without venting the common vacuum enclosure 114.

Figure 3:
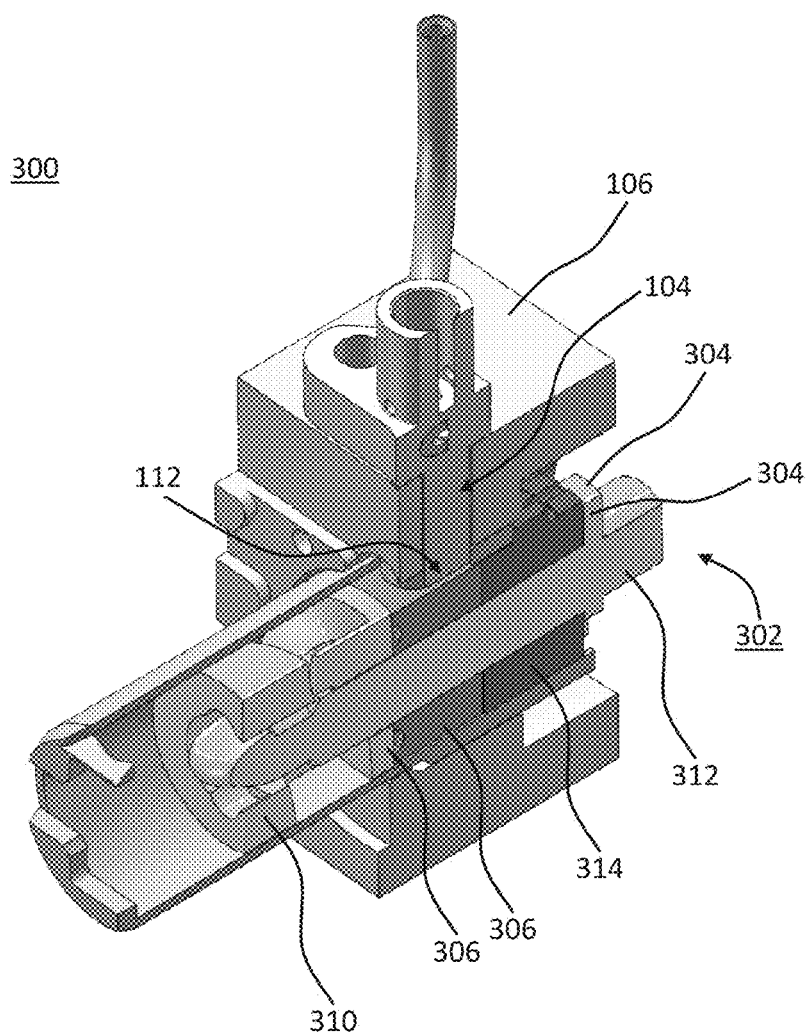
FIG. 3 is a perspective sectional view showing another column-sealing tool according to an embodiment of the invention, disposed adjacent to a transfer line.

FIG. 3 is a perspective sectional view showing a system 300 including a column-sealing tool 302, according to an embodiment of the invention. The general shape of the column-sealing tool 302 is configured to fit into the void immediately adjacent to the outlet (high vacuum) end 112 of the transfer line 104 of a GC-MS system. The column-sealing tool optionally includes an alignment key (not shown), which is used to ensure correct alignment with the transfer line 104 when the tool 302 is inserted into the system 300. Locking features 304 (or engagement structure) are provided at one end of the column-sealing tool 302, for engaging complementary features of a not-illustrated I/R tool, which is used for inserting and retracting the column-sealing tool 302. Also shown in FIG. 3 is a sealing element 306, which is fabricated from a malleable, high temperature material. By way of a few specific and non-limiting examples, the sealing element 306 is fabricated from one of silicone rubber, a fluorinated elastomer, and a polyimide.

Figures 4A, 4B:
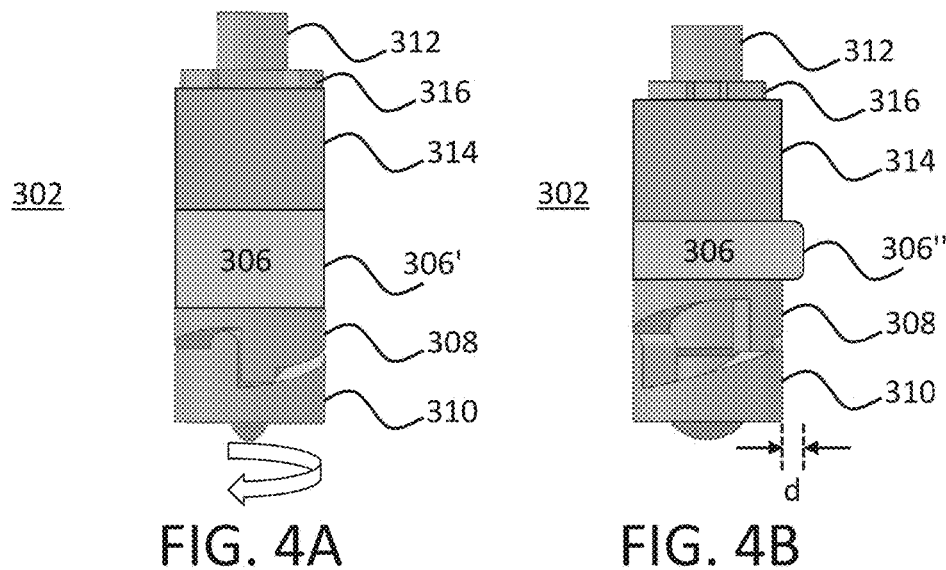
FIG. 4A is a simplified diagram showing the column-sealing tool of FIG. 3 in a non-sealing condition.
FIG. 4B is a simplified diagram showing the column-sealing tool of FIG. 3 in a sealing condition.

Referring also to FIGS. 4A and 4B, the sealing element 306 is actuatable between a non-sealing position 306' (as shown in FIG. 4A) and a sealing position 306" (as shown in FIG. 4B). More particularly, the column-sealing tool 302 includes an actuator, which in this specific example is an internal cam-based actuator comprising a stationary cam 308 and a moving cam 310. The sealing element 306, the stationary cam 308 and the moving cam 310 are mounted on a common shaft 312, along with a guide member 314 and a retaining plate 316. When the moving cam 310 is rotated relative to the stationary cam 308, a spacing therebetween is increased and the sealing element 306 is compressed between the adjacent surfaces of the stationary cam 308 and guide member 314. The guide element 514 is fabricated from a suitable material, such as for instance Vespel SCP 5000. In general, the materials that are used to fabricate the various parts of the column-sealing tool 302 should be able to withstand temperatures greater than 350° C.

During compression, the sealing element swells or bulges along at least one direction, thereby being actuated between the non-sealing position 306' and the sealing position 306". In FIG. 4 the sealing element 306 bulges a distance "d," which is not drawn to scale, but rather it is exaggerated in order to provide a better understanding of the operating principle. In practice, the column-sealing tool 302 is sized-similarly to the void that is created in the heating block 106 when the ion source 102 is removed. The sealing element bulges sufficiently to form the secondary vacuum seal against the outlet end 112 of transfer line 104. As discussed previously with reference to FIGS. 2B and 2C, the ferrule 118 may be removed after the sealing element 206 engages the outlet end 112 of transfer line 104 to form the secondary vacuum seal, and the capillary column 116 may then be decoupled from the system without venting the common vacuum enclosure 114.

Figure 5:
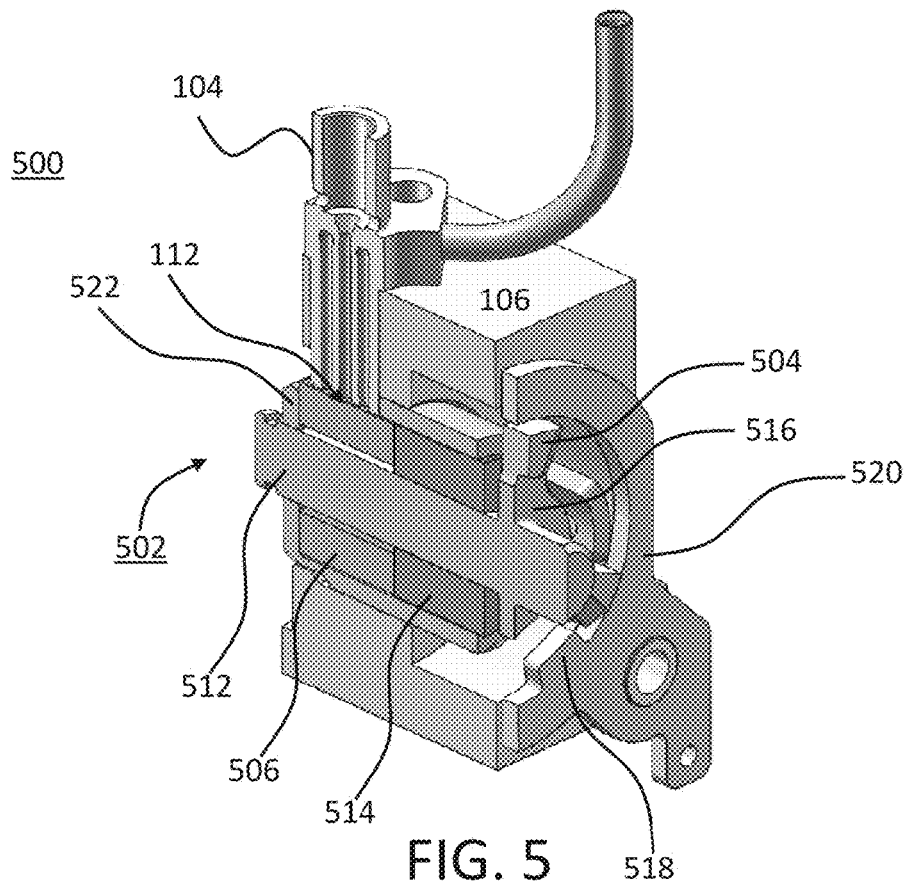
FIG. 5 is a perspective sectional view showing another column-sealing tool according to an embodiment of the invention, disposed adjacent to a transfer line.

FIG. 5 is a perspective sectional view showing a system 500 including a column-sealing tool 502, according to an embodiment of the invention. It is to be understood that the column-sealing tool 502 and the column-sealing tool 302 rely on similar operating principles. In particular, both column-sealing tools 302 and 502 act to compress a sealing element 306 and 506, respectively, in a longitudinal direction along the length of a shaft 312 and 512, respectively. Compression of the sealing element 306 and 506 in the longitudinal direction results in a "bulging-out" of the sealing element 306 and 506 in a direction that is perpendicular to the longitudinal direction. More particularly, the sealing element 306 and 506 bulge outwardly toward the outlet end 112 of the transfer line 104 and form a secondary vacuum seal therewith.

Referring still to FIG. 5, the general shape of the column-sealing tool 502 is configured to fit into the void immediately adjacent to the outlet (high vacuum) end 112 of the transfer line 104 of a GC-MS system. The column-sealing tool 502 optionally includes an alignment key (not shown), which is used to ensure correct alignment with the transfer line 104 when the tool 502 is inserted into the system 500. Locking features 504 (or engagement structure) are provided at one end of the column-sealing tool 502. In particular, the locking features 504 include ramped-tab structures disposed along the periphery of a retaining plate 516. The locking features 504 are arranged to engage complementary ramped-tab structures 518 of a plate 520 configured with the heating block 106.

During use, a not-illustrated I/R tool is used to insert the column-sealing tool 502 into the position that is shown in FIG. 5. An operator inserts the column-sealing tool 502 into the void that is created when the removable ion source 102 is removed, with the application of sufficient pressure to partially compress the sealing element 506 between surfaces of end plate 522 and guide element 514. The sealing element 506 is fabricated from a malleable, high temperature material. By way of a few specific and non-limiting examples, the sealing element 506 is fabricated from one of silicone rubber, a fluorinated elastomer, and a polyimide. The guide element 514 is fabricated from a suitable material, such as for instance Vespel SCP 5000. In general, the materials that are used to fabricate the various parts of the column-sealing tool 502 should be able to withstand temperatures greater than 350° C.

The operator subsequently twists the I/R tool, forcing the ramped-tab locking features 504 of the column-sealing tool 502 to be driven below the complementary ramped-tab features 518, and thereby further compressing the sealing element 506 and causing the sealing element 506 to bulge toward the outlet end 112 of transfer line 104 and form a secondary vacuum seal therewith. Such a ramped-tab design enables the entire column-sealing tool 502, as shown in FIG. 5, to be easily and quickly coupled to and decoupled from the heater block assembly 106 using the I/R tool.

Figure 6:
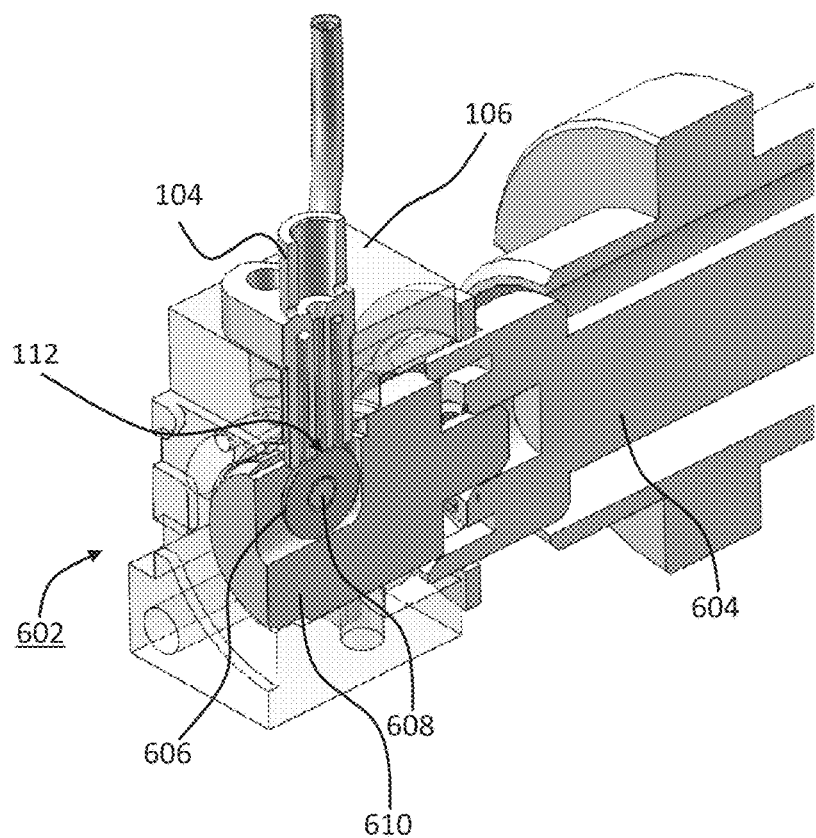
FIG. 6 is a perspective sectional view showing yet another column-sealing tool according to an embodiment of the invention, disposed adjacent to a transfer line.

FIG. 6 is a perspective sectional view showing a system 600 including a column-sealing tool 602, according to an embodiment of the invention. The general shape of the column-sealing tool 602 is configured to fit into the void immediately adjacent to the outlet (high vacuum) end 112 of the transfer line 104 of a GC-MS system. The column-sealing tool 602 optionally includes an alignment key (not shown), which is used to ensure correct alignment with the transfer line 104 when the tool 602 is inserted into the system 600. During use, an I/R tool (604) is used to insert the column-sealing tool 602 into the position that is shown in FIG. 6. More particularly, an operator inserts the column-sealing tool 602 into the void that is created when the removable ion source 102 is removed, with the application of sufficient pressure to cause the wheel-shaped the sealing element 606 to roll over the outlet end 112 of the transfer line 104. The sealing element 606 is fabricated from a malleable, high temperature material and is shaped such that it becomes compressed between the outlet end 112 of the transfer line and a shoulder screw 608, which rotatably mounts the sealing element 606 to a body 610 of the column-sealing tool 602, when the column-sealing tool 602 is fully inserted. The shoulder screw 608 also acts as an axle about which the wheel-shaped sealing element 606 rotates as the column-sealing tool 602 is being inserted. One end of the body 610 of the column-sealing tool 602 includes an engagement structure (not shown). The engagement structure is for removably securing the column-sealing tool 602 within the high vacuum enclosure of the GC-MS system, at a location between the high vacuum end of a transfer line and a mass analyzer of the GC-MS system. By way of a few specific and non-limiting examples, the sealing element 606 is fabricated from one of silicone rubber, a fluorinated elastomer, and a polyimide. In general, the materials that are used to fabricate the various parts of the column-sealing tool 602 should be able to withstand temperatures greater than 350° C.

Figure 7:
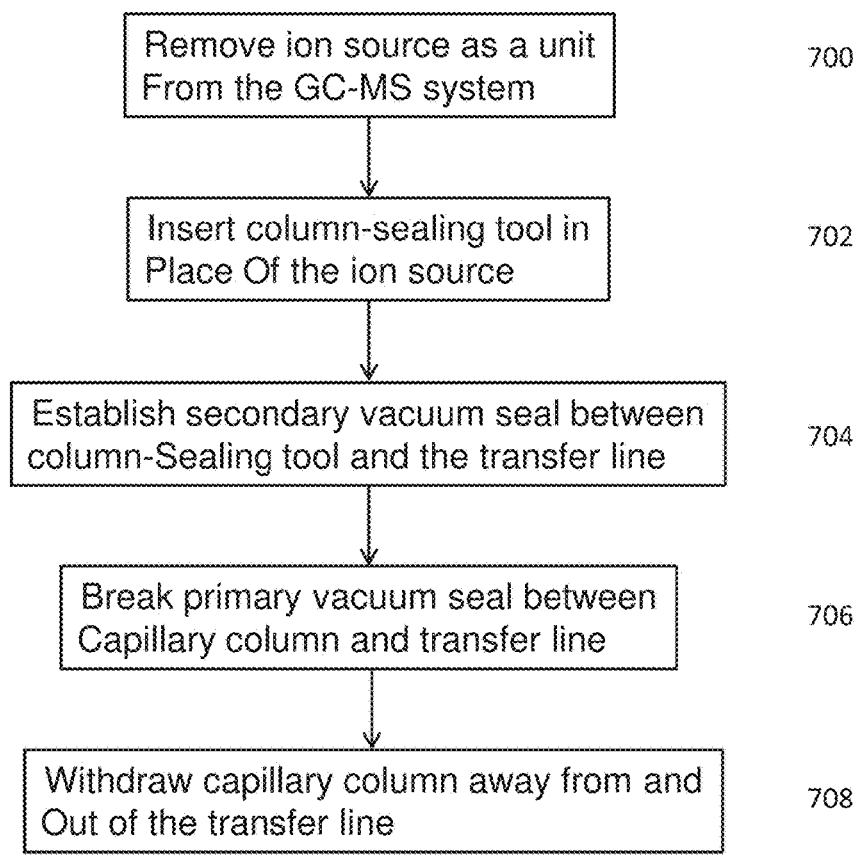
FIG. 7 is a simplified flow diagram for a method according to an embodiment of the invention.

Referring now to FIG. 7, shown is a simplified flow diagram of a method for decoupling a capillary column from a CG-MS system, according to an embodiment of the invention. At 700 a removable ion source is removed as a unit from the GC-MS system. The ion source being disposed, prior to removal, between a high vacuum end of a transfer line and a mass analyzer of the GC-MS system. By way of an example, an I/R tool is used to engage one end of the removable ion source and to subsequently withdraw the removable ion source out of the GC-MC system via a valve system so as to avoid the need to vent a common vacuum enclosure of the GC-MS system. At 702 a column-sealing tool is inserted in place of the ion source. The column-sealing tool having a sealing element that is actuatable between a non-sealing position and a sealing position, and the sealing element being maintained in the non-sealing position during inserting of the column-sealing tool. At 704 the sealing element is actuated from the non-sealing position to the sealing position to form a secondary vacuum seal with the high vacuum or outlet end of the transfer line. At 706, subsequent to establishing the secondary vacuum seal, a primary vacuum seal between the capillary column and an end of the transfer line that is opposite the high vacuum end is broken. For instance, a ferrule that is used to form a seal between the transfer line and the capillary column is loosened and the transfer line is opened to ambient atmospheric pressure. Finally, at 708 the capillary column is withdrawn away from and out of the transfer line. After breaking the primary vacuum seal and removing the column from the transfer line a gas flow rate through the secondary vacuum seal does not exceed 100 ml/minute. In certain implementations a gas flow rate through the secondary vacuum seal does not exceed 50 ml/minute. In certain implementations a gas flow rate through the secondary vacuum seal does not exceed 10 ml/minute. The maximum flow rate that can be tolerated through the secondary vacuum seal depends upon factors including the length of time that is required to perform maintenance on column, as well as the gases that are present in the ambient atmosphere, etc.

Of course, FIG. 7 depicts the steps that are performed during decoupling of a capillary column from a GC-MS system, without venting or cooling the instrument. In order to replace the column after routine maintenance, or in order to couple a different capillary column to the GC-MS system, substantially the same steps 700-708 are performed in the reverse order. Briefly, one end of the capillary column is inserted into the end of the transfer line that is opposite the outlet end. The capillary column is advanced through the transfer line until it makes contact with the sealing element of the column-sealing tool. Advantageously, the sealing element acts as a "stop" for the column and ensures accurate and precise positioning of the capillary column without the need to use specialized tools or provide extensive operator training. Once the column is in the correct position, the ferrule is tightened and the primary vacuum seal is re-established. The sealing element is then actuated to the non-sealing position, thereby breaking the secondary vacuum seal and permitting the column-sealing tool to be removed from the GC-MS system via the valve system. Finally, the ion source is inserted into the GC-MS system via the valve system, and productive operation of the GC-MS system may resume.

While the above description constitutes a plurality of embodiments of the present invention, it will be appreciated that the present invention is susceptible to further modification and change without departing from the fair meaning of the accompanying claims.

What is claimed is:

1. A method for decoupling a capillary column from a gas chromatography-mass spectrometry (GC-MS) system, comprising:
   removing an ion source as a unit from the GC-MS system, the ion source is disposed, prior to removal, between a high vacuum end of a transfer line and an analyzer of the GC-MS system;
   inserting in place of the ion source a column-sealing tool having a sealing element that is actuatable between a non-sealing position and a sealing position, the sealing element being maintained in the non-sealing position during inserting;
   actuating the sealing element from the non-sealing position to the sealing position to form a secondary vacuum seal with the high vacuum end of the transfer line;
   subsequent to establishing the secondary vacuum seal, breaking a primary vacuum seal between the capillary column and an end of the transfer line that is opposite the high vacuum end; and
   withdrawing the capillary column away from and out of the transfer line.

2. The method of claim 1, comprising:
   inserting an outlet end of a capillary column into the transfer line, via the end that is opposite the high vacuum end, and advancing the capillary column until the outlet end contacts the sealing element;
   establishing the primary vacuum seal between the capillary column and the end of the transfer line that is opposite the high vacuum end;
   actuating the sealing element from the sealing position to the non-sealing position to break the secondary vacuum seal;
   removing the column-sealing tool from the GC-MS system; and
   inserting the ion source between the high vacuum end of the transfer line and the analyzer of the GC-MS system.

3. The method of claim 2, wherein each of the steps is performed absent venting a common enclosing vacuum.

4. The method of claim 3, comprising maintaining at least a heating element of the GC-MS system at a same temperature that is set when the GC-MS system operates in an analyzing mode.

5. The method of claim 3, wherein the step of removing and the step of inserting comprises using a vacuum interlock for transferring the ion source and the column-sealing tool, respectively, between ambient atmosphere and high vacuum.

6. The method of claim 1, wherein after breaking the primary vacuum seal a gas flow rate through the secondary vacuum seal does not exceed 100 ml/minute.

7. The method of claim 1, wherein after breaking the primary vacuum seal a gas flow rate through the secondary vacuum seal does not exceed 50 ml/minute.

8. The method of claim 1, wherein after breaking the primary vacuum seal a gas flow rate through the secondary vacuum seal does not exceed 10 ml/minute.

\* \* \* \* \*